(12) United States Patent
Farin (10) Patent No.: US 10,307,264 B2
(45) Date of Patent: *Jun. 4, 2019

(54) SPINE SURGERY DEVICE (71) Applicant: AZADEH FARIN WALD, M.D., INC., A Medical Corporation, Rolling Hills, CA (US)

(72) Inventor: Azadeh Farin, Rolling Hills, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/406,563

(22) Filed: Jan. 13, 2017

(65) Prior Publication Data

US 2017/0119546 A1    May 4, 2017

Related U.S. Application Data (63) Continuation of application No. 14/798,127, filed on Jul. 13, 2015, now Pat. No. 9,545,319, which is a continuation of application No. 13/576,767, filed as application No. PCT/US2011/023502 on Feb. 2, 2011, now Pat. No. 9,078,769.

(Continued)

(51) Int. Cl.
*A61F 2/44* (2006.01)
*A61F 2/30* (2006.01)
*A61B 17/02* (2006.01)
*A61F 2/28* (2006.01)

(52) U.S. Cl.
CPC ........ *A61F 2/4465* (2013.01); *A61F 2/30771* (2013.01); *A61F 2/442* (2013.01); *A61B 2017/0256* (2013.01); *A61F 2/30907* (2013.01); *A61F 2002/2817* (2013.01); *A61F 2002/2835* (2013.01); *A61F 2002/3055* (2013.01); *A61F 2002/30405* (2013.01); *A61F 2002/30448* (2013.01); *A61F 2002/30484* (2013.01); *A61F 2002/30556* (2013.01); *A61F 2002/30579* (2013.01); *A61F 2002/30841* (2013.01);

(Continued)

(58) Field of Classification Search
CPC ...... A61F 2/4405; A61F 2/442; A61F 2/4425; A61F 2/46; A61F 2/4611; A61F 2002/30362; A61F 2002/30405; A61F 2002/30411; A61F 2002/30484; A61F 2002/30518; A61F 2002/30537; A61F 2002/30538; A61F 2002/3054; A61F 2002/30545; A61F 2002/3055; A61F 2002/30553; A61F 2002/30555; A61F 2002/30556; A61F 2002/4495; A61F 2002/448

See application file for complete search history.

(56) References Cited

U.S. PATENT DOCUMENTS

2004/0249461 A1* 12/2004 Ferree ............... A61F 2/2846
                                                      623/17.11
2005/0256576 A1* 11/2005 Moskowitz ......... A61F 2/441
                                                      623/17.12

(Continued)

*Primary Examiner* — Lynnsy M Summitt
(74) *Attorney, Agent, or Firm* — Steptoe & Johnson LLP (57) ABSTRACT

The invention relates to a device intended to replace or partially replace one or more vertebral bodies or intervertebral discs in the cervical, thoracic or lumbar spine, and includes methods for its use and deployment. The invention may be used to restore biomechanical parameters correlating with improved patient outcomes and also involves a method for a more effective discectomy or corpectomy prior to graft deployment.

16 Claims, 9 Drawing Sheets

Related U.S. Application Data

(60) Provisional application No. 61/300,580, filed on Feb. 2, 2010.

(52) U.S. Cl.
CPC ............... *A61F 2002/30904* (2013.01); *A61F 2002/30914* (2013.01)

(56) References Cited

U.S. PATENT DOCUMENTS

| | | | |
|---|---|---|---|
| 2007/0156026 A1* | 7/2007 | Frasier | A61B 17/02 600/224 |
| 2007/0198089 A1* | 8/2007 | Moskowitz | A61F 2/442 623/17.11 |

* cited by examiner

SPINE SURGERY DEVICE

CROSS-REFERENCE TO RELATED APPLICATIONS

This application is a continuation of U.S. application Ser. No. 14/798,127, filed Jul. 13, 2015, now U.S. Pat. No. 9,545,319, which is a continuation of U.S. application Ser. No. 13/576,767, filed Aug. 2, 2012, now U.S. Pat. No. 9,078,769, which is the National Phase of International Application PCT/US11/23502, filed Feb. 2, 2011, which designated the U.S. and that International application was published under PCT Article 21 (2) in English. This application also includes a claim of priority under 35 U.S.C. § 119(e) to U.S. provisional patent application No. 61/300,580, filed Feb. 2, 2010. All of the above applications are incorporated by reference in their entirety.

BACKGROUND

1. Field of the Invention

The present invention is directed generally to a device intended to replace or partially replace a vertebral body or intervertebral disc in the cervical, thoracic or lumbar spine, as well as methods for its use and deployment.

2. Description of the Related Art

All publications cited herein are incorporated by reference in their entirety to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

Various devices are known in the art for the replacement or partial replacement of vertebral bodies or intervertebral discs in the cervical, thoracic, and lumbar spine. These are often used to replace, restore, correct, augment, strengthen, support or maintain height of an unstable, fractured, collapsed, damaged, degenerated or degraded vertebral body segment or intervertebral disc space or portion thereof, which has compromised integrity due to cancer or tumor or other lesion including hematalogic, metabolic or other systemic processes affecting spinal structures; is unstable because of trauma or any other process compromising integrity of ligaments, soft tissues, or osseous structures; or is characterized by a degenerative or deforming process including but not limited to congenital deformities, degenerative disease, kyphosis, spinal deformity/scoliosis, or spondylolisthesis. The device described herein is also relevant and applicable as it pertains to any spinal segment that has a surgical indication based on patient presentation and surgeon's judgment with no limitations otherwise. Cervical neck pain or axial back pain with or without radicular symptoms are frequently symptoms, and neurologic deficit involving loss of strength or sensation is frequently a sign, of such conditions. Further devices and methods are known in the art for performing the surgical procedures required to effectuate the removal of disc tissue or osseous structures and achieve the insertion and placement of some type of spinal segment replacement device.

The number of thoracic and lumbar fusions being performed has increased dramatically during the past ten years, far in excess of what would be expected proportionately considering population growth and aging demographics alone. Spine surgeons are now seeing many patients return post-fusion with symptoms limiting their professional, personal, and social functionality that stem from a fusion performed in the past without appropriate consideration for the biomechanical principle of sagittal balance and restoration of lumbar lordosis. The vast majority of thoracic and lumbar fusions are currently performed through a posterior approach, through a posterolateral fusion that does not involve interbody grafting or via a posterior lumbar interbody fusion ("PLIF") cage (i.e., the disc space is accessed bilaterally and extensive nerve root retraction is required) or through a transforaminal lumbar interbody fusion ("TLIF") with a TLIF cage (i.e., the spine is approached posteriorly similar to the PLIF, but unilaterally more from the side of the spinal canal through the foramen, potentially reducing nerve root retraction required to access the disc). The traditional posterior approach is well-tolerated by patients but can restrict the amount of disc material that can be removed safely and more importantly restricts the size and type of currently available cage that can be placed through this small opening, an orifice limited by the degree of traction that can be placed on critical nerve roots or otherwise limited by the window of access to the disc space. Current grafts available for insertion via a posterior approach are hampered by subphysiologic degrees of lordosis and endplate coverage, compared with anatomically appropriate lordotic grafts with larger endplate coverage. Given currently available technology, marketed grafts and described techniques, these subpar grafts are inserted from a posterior trajectory and do not restore appropriate lumbar lordosis or sagittal balance. Up to now, limited space afforded by a posterior approach because of proximity of critical nerve roots has seemingly and supposedly limited the size and type of graft that has been marketed as available for posterior insertion. Insertion of a smaller and biomechanically misproportioned graft, as necessitated by current grafts that are available for insertion from a posterior approach at this time, may lead to a higher rate of pseudoarthrosis and lower rate of fusion, since surface area contact of endplate vs. graft is less than that obtained during an anterior approach where a larger and more biomechanically appropriate graft can be implanted. Anatomically and biomechanically, the posterior approach to discectomy and fusion, using currently available implants, is further limited in its ability to reestablish optimal lumbar lordosis and restore global sagittal balance (global sagittal imbalance is defined as a distance of greater than 50 mm from the C7 sagittal vertical axis and the S1 sagittal vertical axis), key biomechanical phenomena proven in the literature to be critical to successful patient outcomes. See, e.g., S D Glassman et al., "The impact of positive sagittal balance in adult spinal deformity," Spine 30(18):2024-9 (2005).

Although the posterior approach to the spine can be faster, easier and less risky in most patients, many surgeons find that the anterior approach to the spine and placement of an Anterior Lumbar Interbody Fusion ("ALIF") cage is more advantageous because of larger endplate coverage and increased degree of lordosis of the graft that can be implanted, thus achieving greater graft-endplate surface area contact and better biomechanical establishment of lumbar lordosis and restoration of sagittal balance. This procedure is performed from the ventral aspect of the spine, usually through a 3-5 inch incision in the lower left abdominal area. This incision may involve cutting through, and later repairing, the muscles in the lower abdomen, retracting the peritoneum, and retracting the great vessels and ureter. This enables total direct discectomy and placement of a large lordotic cage with generous endplate contact, resulting in excellent fusion rates, and superb reestablishment of lumbar lordosis and sagittal balance. However, the ALIF is somewhat limited in its employment because it requires access to the anterior part of the spine to be provided by a trained vascular or other qualified surgeon before the spine surgeon can perform discectomy and fusion (whereas the posterior approach does not require an approach surgeon). The anterior approach can lead to life-threatening consequences, such as loss of limb and life-threatening hemorrhage, as well as retrograde ejaculation in men, impairing their fertility. The anterior approach may also require further posterior stabilization subsequently, thus leaving patients with an incision from the front of the abdomen and a second incision from the back. Finally, the anterior approach carries a risk of abdominal pseudohernia or true hernia. These potential complications and hassles explain why most spine surgeons prefer the more practical posterior approach and use currently available grafts, but compromise with fusion rates, lordosis reestablishment and sagittal balance correction that is inferior to an anterior approach with a more biomechanically sound graft.

The ideal then would be a graft that can be inserted from a posterior approach (which carries the least risk of morbidity for the patient) but achieves similar benefits to grafts currently available for anterior insertion in terms of restoring sagittal balance and lumbar lordosis. While there are some devices known in the art that are configured for posterior insertion while seeking increased disc and intervertebral height in excess of that traditionally achieved by grafts used in the past during the posterior approach, these devices each suffer from their own limitations and do not correct for the biomechanical shortcomings of current grafts as described above.

There thus remains a need in the art for a device that is configured substantially for posterior insertion (but that can indeed be inserted from an anterior or lateral trajectory as well), and that incorporates the superior biomechanical advantages of an ALIF-type deployment device (e.g., restoring anatomic degree of lumbar lordosis and sagittal balance and improving graft-endplate contact in order to improve fusion rates), while obviating various physiological, mechanical and practical challenges of placement that would otherwise accompany placement from an anterior trajectory. The graft should be placed after thorough and extensive discectomy with minimal risk of harming critical neurovascular structures by way of a protected portal. Described herein is a device and method that simultaneously accomplishes the above.

SUMMARY

In an embodiment, the invention includes an apparatus, comprising: a first element having a top and a bottom; a second element having a top and a bottom; one or more bridging structures, each in mechanical communication with both the first element and the second element, wherein upon actuation of the one or more bridging structures, the first element and the second element separate from one another; and a lordotic expander, wherein upon actuation of the lordotic expander, the top and the bottom of the first element expand apart from one another. The one or more bridging structures may each comprise complementary male and female screw threading. The apparatus may be generally bullet-shaped. The lordotic expander may be configured to be actuated by a series of rotational clicks. Each of said rotational clicks may represent an approximately 5.degree. increase in lordosis when said apparatus is inserted and deployed in an intervertebral space. The first element may be configured to be placed in the posterior region of an intervertebral space following its deployment in a spine surgery procedure. The second element may be configured to be placed in the anterior region of an intervertebral space following its deployment in a spine surgery procedure. The top of the first element and/or the top of the second element and/or the bottom of the first element and/or the bottom of the second element may independently comprise a surface treatment to reduce migration following insertion and deployment of the apparatus in an intervertebral space. The surface treatment may comprise spikes, teeth or an adhesive. The apparatus may be configured to mechanically communicate with a tool, whereby actuation of the tool causes actuation of the one or more bridging structures. The apparatus may be configured to mechanically communicate with a tool, whereby actuation of the tool causes actuation of the lordotic expander. The apparatus may be adapted for insertion into an intervertebral space through a handle of a distractor tool.

In another embodiment, the invention includes, in combination, the aforementioned apparatus and a distractor tool, the distractor tool comprising: a handle; and an expansion mechanism attached to the handle, the expansion mechanism to controllably expand or retract in both the anterior-posterior direction and the rostral-caudal direction within an intervertebral space. The expansion mechanism may further comprise a first pair of blades to controllably expand or retract in the anterior-posterior direction, and a second set of blades to controllably expand or retract in the rostral-caudal direction.

In another embodiment, the invention includes, in combination, the aforementioned apparatus and a mesh structure to contain a quantity of a material, a graft material or a fusion-promoting chemical or protein. The mesh structure may be incorporated within a space created between the first element and the second element following insertion and deployment of the apparatus. The apparatus may be encapsulated within the mesh structure.

In another embodiment, the invention includes a method, comprising: providing an apparatus, comprising: a first element having a top and a bottom, a second element having a top and a bottom, one or more bridging structures, each in mechanical communication with both the first element and the second element, wherein upon actuation of the one or more bridging structures, the first element and the second element separate from one another, and a lordotic expander, wherein upon actuation of the lordotic expander, the top and the bottom of the first element expand apart from one another; inserting the apparatus into an intervertebral space; actuating the one or more bridging structures; and actuating the lordotic expander. Prior to inserting the apparatus into the intervertebral space, the method may further comprise removing an intervertebral disc, debris, soft tissues or osseous structures from the intervertebral space. Inserting the apparatus into the intervertebral space may further comprise: providing a distractor tool comprising a handle and an expansion mechanism attached to the handle, the expansion mechanism to controllably expand or retract in both the anterior-posterior direction and the rostral-caudal direction within an intervertebral space; expanding the expansion mechanism; and repositioning the apparatus through the handle and into the intervertebral space.

BRIEF DESCRIPTION OF THE DRAWING

Exemplary embodiments are illustrated in referenced figures. It is intended that the embodiments and figures disclosed herein are to be considered illustrative rather than restrictive.

DETAILED DESCRIPTION

All references cited herein are incorporated by reference in their entirety as though fully set forth. Unless defined otherwise, technical and scientific terms used herein have the same meaning as commonly understood by one of ordinary skill in the art to which this invention belongs. One skilled in the art will recognize many methods and materials similar or equivalent to those described herein, which could be used in the practice of the present invention. Indeed, the present invention is in no way limited to the methods and materials described.

The invention relates to a device intended to replace or partially replace one or more vertebral bodies or intervertebral discs in the cervical, thoracic or lumbar spine. The device is configured to be inserted through a posterior approach and may require a spine surgeon only, thereby obviating the need for an anterior approach and its associated complications. Several additional features of the device set it apart from other cages inserted through a posterior approach; for instance, and among other things, it may be introduced through a unique posterior insertion technique allowing for an extensive discectomy through a protected portal that safeguards the neural elements posteriorly and vascular elements anteriorly; the device may eventually expand to approximate the size of an ALIF cage with superior endplate contact and fusion rate; and the device may enable reestablishment of lumbar lordosis from 0 to 15 degrees or other various degrees and can help reestablish global sagittal balance. The device can be inserted through a traditional small posterior approach to the disc space or vertebral body that accommodates the initial pre-deployment compact size of the cage, which is then expandable not only in rostral-caudal height/degrees of lordosis anteriorly, but also expandable in the anterior-posterior direction. These features are illustrated in the accompanying drawings, and are currently not commercially available through other cages and similar devices.

Figure 1:
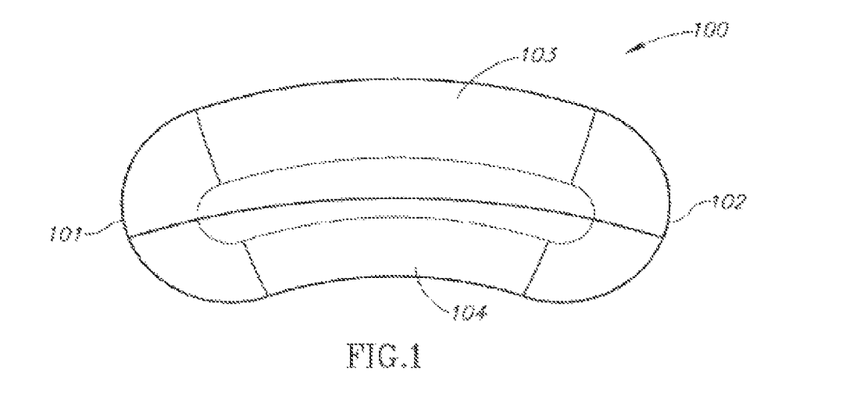
FIG. 1 depicts a top view of a device in a closed position (e.g., prior to surgical insertion), in accordance with an embodiment of the present invention.
Figure 2:
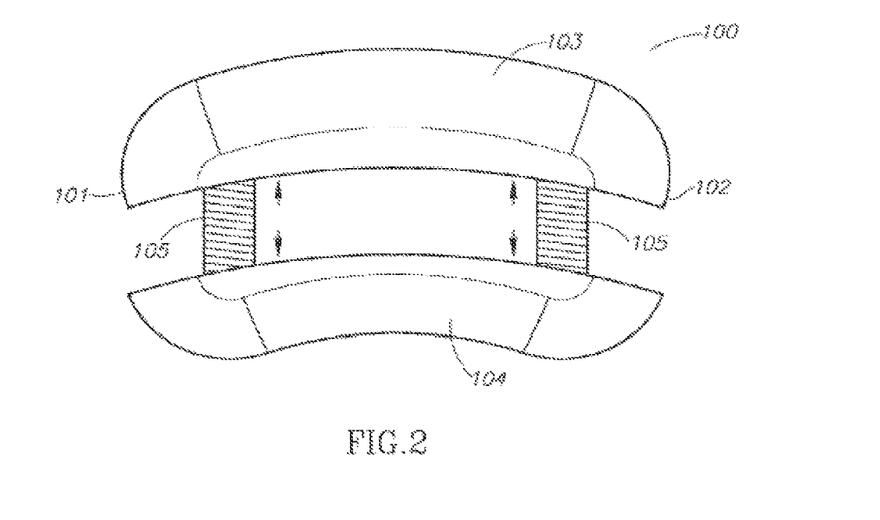
FIG. 2 depicts a top view of a device that has been expanded in the anterior-posterior direction (arrows illustrate direction of anterior-posterior expansion), in accordance with an embodiment of the present invention.
Figure 3:
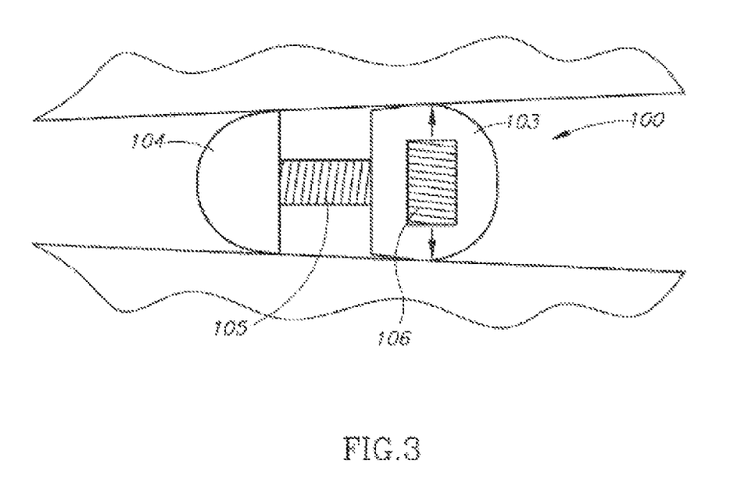
FIG. 3 depicts a sagittal, cross-sectional view of a device that has been expanded in the anterior-posterior direction and wherein arrows depict lordotic expansion, in accordance with an embodiment of the present invention.
Figure 4A:
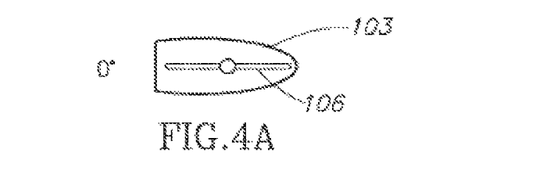
FIGS. 4(A)-(D) depicts a cross-sectional view of an internal mechanism for lordotic expansion of a device, in accordance with an embodiment of the present invention.
Figure 4B:
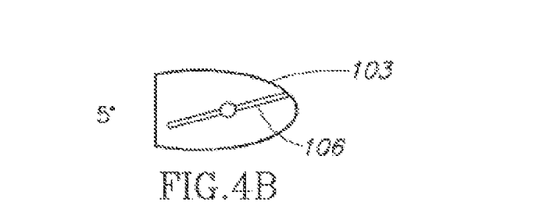
Figure 4C:
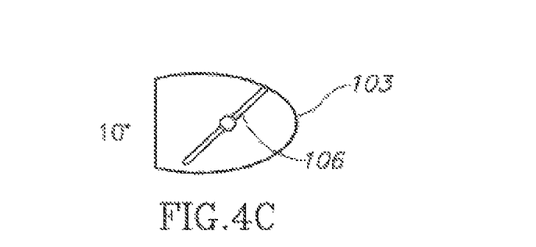
Figure 4D:
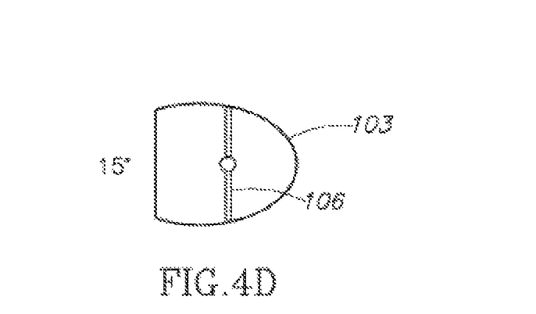

In one embodiment, the device 100 is illustrated in FIGS. 1-3, which depict a top view of the device in compact form prior to in situ deployment (FIG. 1), a top view of the device following in situ deployment and anterior-posterior expansion (FIG. 2), and a sagittal cross-sectional view of the device following both in situ deployment, anterior and posterior expansion and lordotic expansion (FIG. 3). The device 100 is intended for the replacement or partial replacement of a collapsed, degenerated, damaged or unstable vertebral body or intervertebral disc or portion thereof.

The device 100 may be generally bullet-shaped at one or both of its ends 101, 102 (the device 100 illustratively depicted in the Figures is bullet-shaped at both ends). This may aid in insertion of the device 100 into the interbody space, which may follow partial or total discectomy or corpectomy or other substantial clearing of tissue, debris and/or other material from the interbody space. The device 100 may incorporate two elements that are connected; a first element 103 that is configured to remain in the anterior region of the interbody space following insertion and deployment, and a second element 104 that is configured to remain in the posterior region of the interbody space following insertion and deployment. As used herein, "deployment" refers to the mechanical process by which the first element 103 and second element 104 are distracted from one another into their desired locations but still connected via bridging structures 105 to each other, and "lordotic expansion" refers to the mechanical process by which the first element 103 is expanded in the rostral-caudal direction so as to impart the desired angle of lordosis to that segment of the spine.

Anterior-posterior deployment and lordotic expansion of the device 100 may each be effectuated by actuation of a single or more tools that are adapted to mechanically interact with the device 100 to achieve each of these results. In each case, the tool(s) can be controlled by the surgeon. This may be accomplished, for instance, through actuation of a mechanical or electronic mechanism on or in communication with the tool(s) to create the desired result. In the case of deployment, actuation of the tool(s) causes the first element 103 and second element 104 to separate from one another to either a single predetermined distance or a distance that may be controlled by the surgeon depending on a variety of factors that will be appreciated by those of skill in the art (e.g., configuration and structure of the disc space, bone quality of endplate, extent of discectomy, etc.). Separation of the first element 103 and the second element 104 from one another is illustratively depicted in FIG. 2.

One or more bridging structures 105 may cause deployment by operating to drive the first element 103 and the second element 104 away from one another through use of the aforementioned tool(s). The bridging structures 105 may comprise any number of mechanical components to achieve this desired function, as will be readily apparent to those of skill in the art. Simply by way of example, the bridging structures 105 may include complementary male and female screw threading, such that the rotation of particular elements within the bridging structures 105 forces the first element 103 and second element 104 apart from one another. Alternatively, the bridging structures 105 may comprise a peg and groove system.

A lordotic expander 106 may operate to increase the overall "height" of the first element 103 in the rostral-caudal direction, again, through use of the aforementioned single or multiple tools. In alternate embodiments (not shown), a second lordotic expander that operates either together with or independently of the lordotic expander 106 in the first element 103 may be included in the second element 104. As illustrated in FIG. 4, the lordotic expander 106 may actuate via a series of rotational "clicks," whereby each "click" further increases the height of at least a portion of the first element 103. In FIG. 4, four such settings are illustrated, whereby a final lordosis of each of 0.degree., 5.degree., 10.degree. and 15.degree. can be obtained (or other proscribed degrees as may be desirable). In alternate embodiments of the device 100, a greater or fewer number of options for angles of final lordotic expansion may be permitted. In any case, lordotic expansion causes the top and bottom of the second element 104 to move apart from one another by a distance of anywhere from 1 mm to as many as 15 cm, depending upon the number of vertebral bodies being replaced, the degree of lordosis sought to be achieved, or any number of other physiologic or biomechanical factors that would be readily appreciated by those of skill in the art. Thus, in various embodiments of the present invention, an expansion range for the lordotic expander 106 can be 1 mm-10 mm, 1 mm-1 cm, 10 mm-2 cm, 1 cm-6 cm, 1 cm-10 cm, 5 cm-15 cm, or any other range of expansion from as little as 1 mm on the low end to as much as 15 cm at the high end. Moreover, expansion of lordotic expander 106 may occur in a manner whereby the top and bottom surfaces remain in parallel planes relative to one another once the lordotic expander 106 has been actuated, or, in an alternate embodiment, the top and bottom surfaces do not remain in parallel planes relative to one another following actuation of the lordotic expander 106.

Figure 7A:
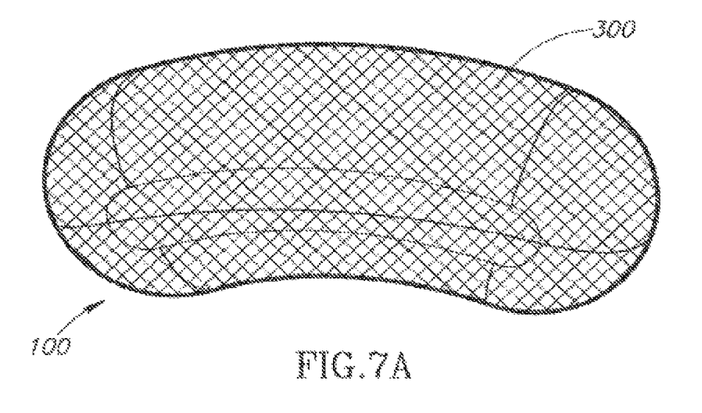
FIG. 7A depicts a perspective view of a mesh structure encapsulating a device in a pre-deployment top view.
Figure 7B:
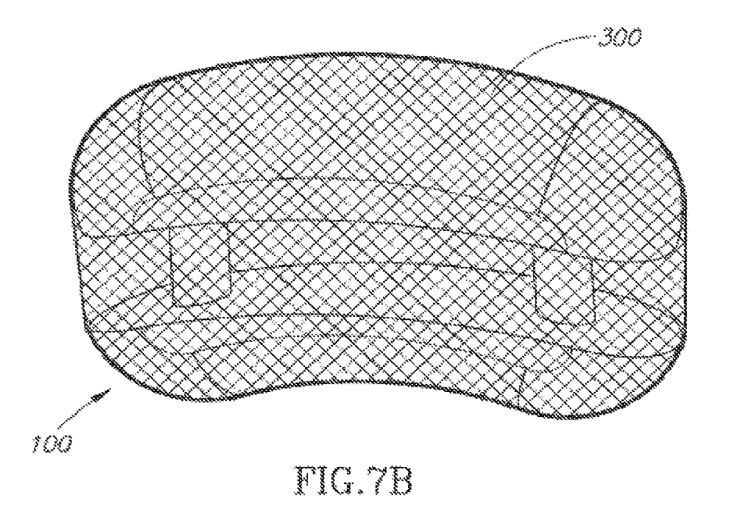
FIG. 7B depicts a top view perspective of the device shown in FIG. 7A in a post deployment configuration of a device after anterior-posterior expansion, in accordance with various embodiments of the present invention.
Figure 7C:
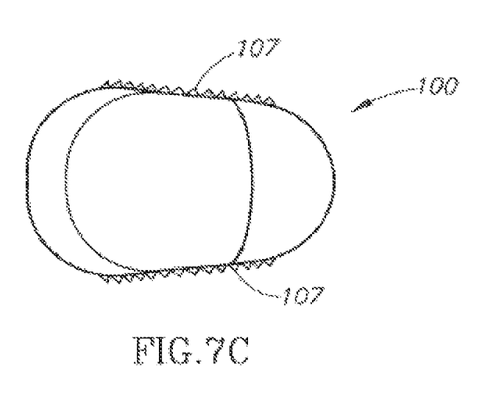
FIG. 7C depicts a sagittal or side perspective view of the device shown in FIG. 7A with spikes after anterior-posterior and lordotic deployment, in accordance with various embodiments of the present invention.
Figure 7D:
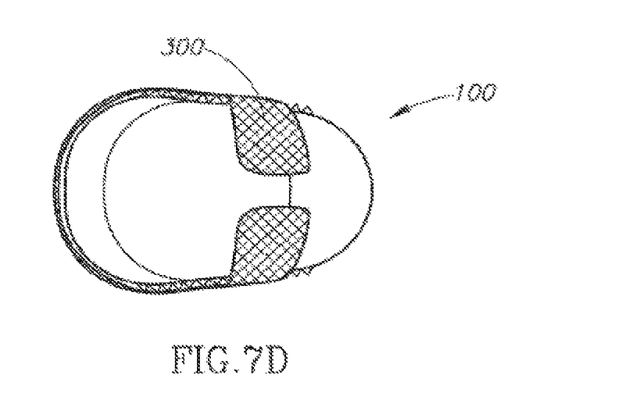
FIG. 7D depicts a top view of the device as deployed in FIG. 7C with a mesh structure shown atop the device, in accordance with various embodiments of the present invention.
Figure 7E:
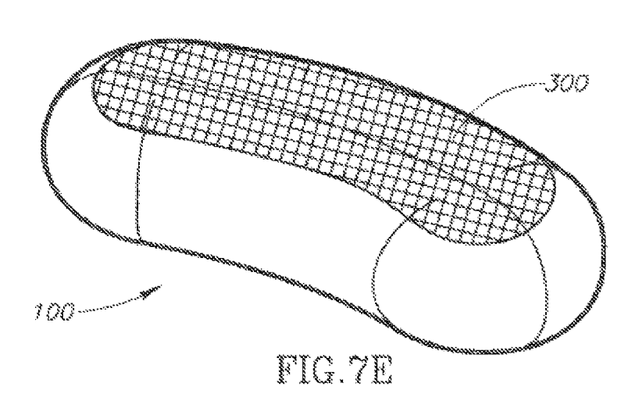
FIG. 7E depicts the device shown in FIG. 7C having pre-anterior-posterior deployment, in accordance with various embodiments of the present invention.
Figure 7F:
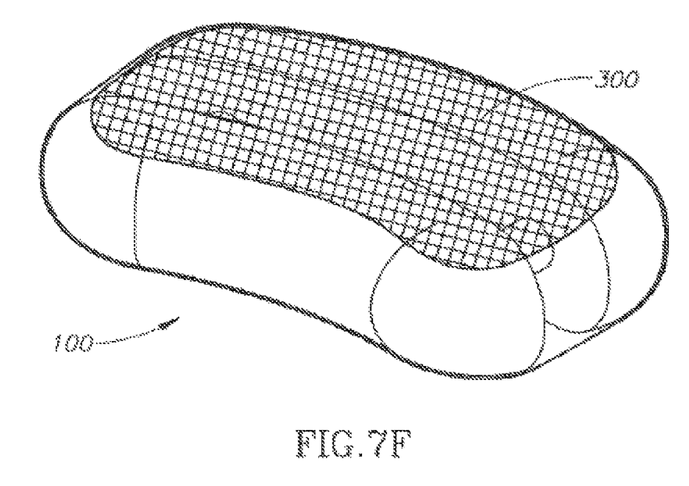
FIG. 7F depicts the device shown in FIG. 7C having post-anterior-posterior deployment, in accordance with various embodiments of the present invention.
Figure 8:
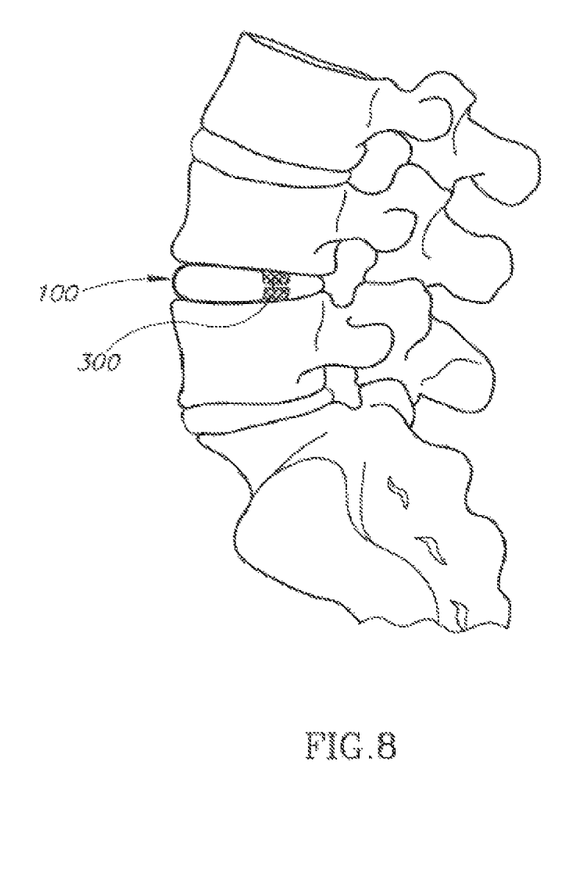
FIG. 8 depicts a side or sagittal, perspective view of a device, post-anterior-posterior and lordotic deployment and with a mesh structure attached to it, expanded post-deployment in an intervertebral space, in accordance with an embodiment of the present invention.

The surfaces of the first element 103 and second element 104 that are intended to come into contact with the vertebrae following insertion and deployment may be configured so as to reduce migration. For instance, these surfaces may include spikes, teeth or other mechanical features 107 (FIG. 7C) or they might include or be impregnated with adhesives, substrates that promote fusion to the endplate, or other biochemical elements (not shown) that prevent or at least reduce the likelihood of migration following surgery and may promote fusion once final position is accepted by the surgeon. By way of example, these might include mechanical, anatomic, morphogenic, or chemical components that promote a graft residing in a biomechanically appropriate position initially selected by a surgeon and in a manner that retards migration.

In a further embodiment of the invention, one or more expandable balloon and/or mesh structures may be included to biomechanically support the device 100 and to contain a volume of material (e.g., graft material) or other fusion-promoting chemical/protein to enhance fusion following surgery. Any number of such structures and corresponding materials are known to those of skill in the art and can be implemented in combination with the device 100 by routine procedures. By way of example, a mesh structure 300 may be incorporated within the space created between the first element 103 and second element 104 following deployment. Alternatively, the entire device 100 may be encapsulated within a mesh structure 300 (FIG. 7A, 7B), or a mesh structure 300 can be configured partially or entirely alongside, within, atop or otherwise nearby the device 100 when deployed (FIGS. 7D, 7E, 7F and 8). Depending upon the configuration, the mesh structure 300 may also expand in the manner and directions that the device 100 expands; for instance, in both the anterior-posterior direction (as may be achieved with the device 100 by actuation of the bridging structures 105) as well as the rostral-caudal direction (as may be achieved with the device 100 by actuation of the lordotic expander 106).

Figure 5:
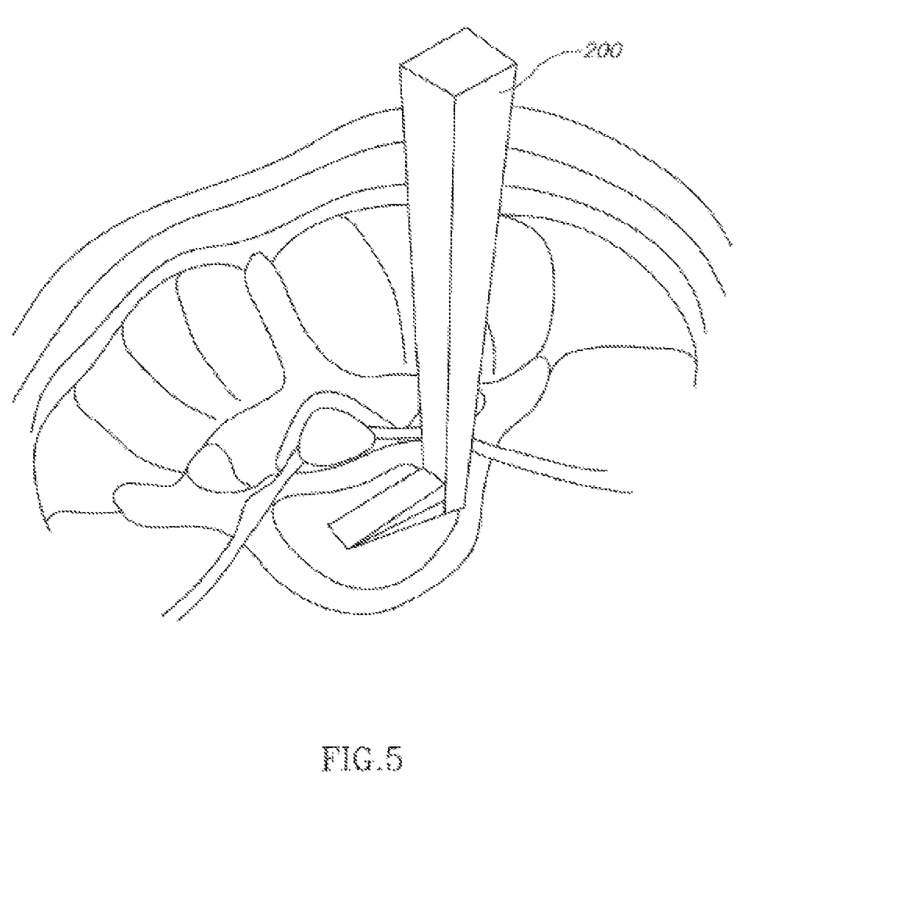
FIG. 5 depicts insertion of a distractor tool, in accordance with an embodiment of the present invention.
Figure 6A:
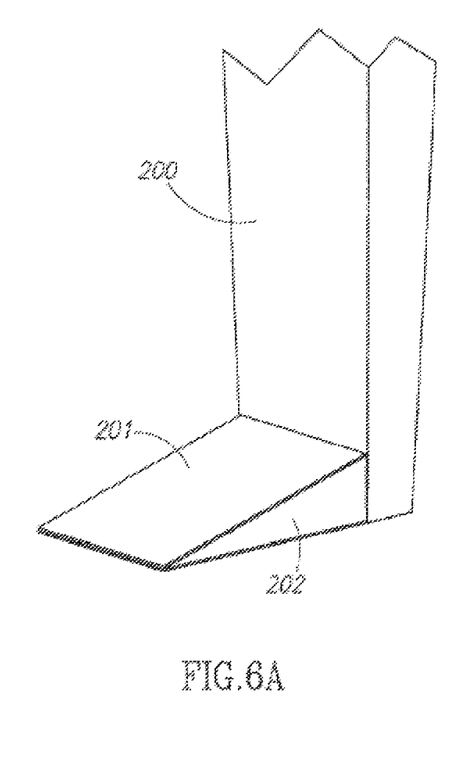
FIG. 6A depicts the deployment end of a distractor tool in a closed position, in accordance with an embodiment of the present invention.
Figure 6B:
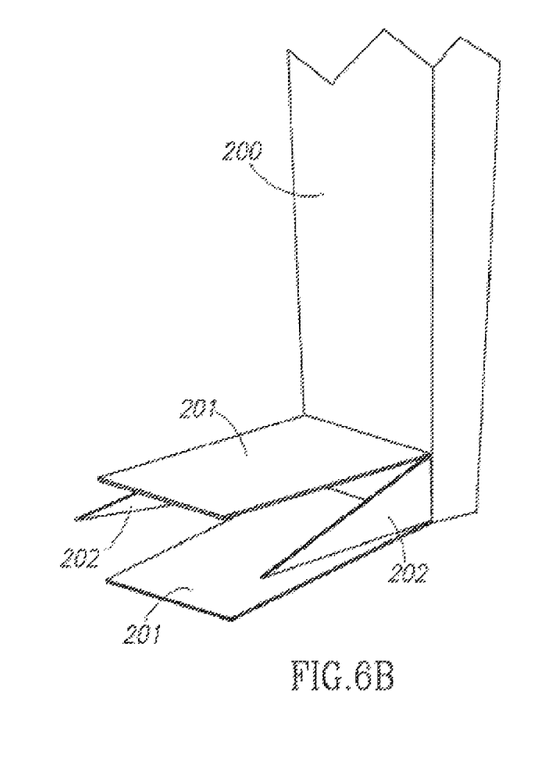
FIG. 6B depicts the deployment end of a distractor tool in an open position, in accordance with an embodiment of the present invention.

With regard to the tools referenced above, as illustrated in FIG. 5, one embodiment of the invention includes a distractor tool 200 configured for insertion into the interbody space. In an embodiment, the distractor tool includes a four-blade expansion mechanism 201, 202 at the end designed for introduction into the interbody space. In alternate embodiments, the expansion mechanism can have any number of geometric configurations, such as triangular, rectangular, square, rhomboidal or trapezoidal. Upon actuation of the tool, a first pair of blades 202 can controllably expand or retract in the anterior-posterior direction safely without overexpansion and can self-maintain various degrees of expansion through mechanical means while the surgeon continues to operate, thereby protecting the great vessels and neural structures respectively during discectomy. A second pair of blades 201 can controllably expand or retract in the rostral-caudal direction without violating the endplates to increase disc and foraminal height. Expansion of the distraction tool in the rostral-caudal direction may include the use of a series of sequentially larger asymmetric metal disc space dilators that can be malletted through the distractor to achieve lordotic end plate distraction without violating the end plate or a variety of other mechanical means to achieve the same. All four blades can self-retain a variable degree of expansion safely and can be guarded against overdistraction via particular mechanical mechanisms. In various embodiments of the distractor tool, the two pairs of blades 201, 202 may be operated either together or independently from one another. In various embodiments of the distractor tool, the two pairs of blades confer protection of critical surrounding neurovascular structures, including nerve roots and iliac arteries and veins, during a surgical procedure.

The distractor tool 200 may be configured to operate with a disc removal tool. The disc removal tool is adapted to remove disc (e.g., under fluoroscopic guidance) and gently decorticate bone as an option if desired given quality of the endplate to prepare a fusion bed for the device 100. In one embodiment, the disc removal tool includes a rotating shaver and a vacuum suction device, thereby allowing a surgeon to mechanically disrupt disc and related materials in the interbody space or in the intervertebral space and simultaneously remove these items from the interbody space by operation of the vacuum. In one embodiment, the disc removal tool is configured to operate in concert with the distractor tool; for instance, once the distractor tool is inserted to increase disc and foraminal height and protect neurovascular structures, the disc removal tool can be inserted and operated through the hollow neck of the distractor tool and thus reach the interbody space. In operation, the disc removal tool may have a variety of safety features, including, by way of example, a feature that results in an alarm when the disc removal tool, in operation, contacts cortical bone, so the surgeon can avoid breach of the cortex.

In yet another embodiment of the invention, the device 100 is configured to be inserted into the interbody space through the neck of the distractor tool. In another embodiment of the invention, one or more additional tools (such as an inserter tool) are configured to operate through the neck of the distractor tool to position, deploy and/or actuate various mechanical features of the device 100. For instance, an inserter tool may be used to actuate the bridging structures 105 and/or the lordotic expander 106. In one embodiment of the invention, a single tool (or possibly multiple tools) may be used for cage insertion, expanding in the anterior-posterior direction, lordotic expansion in the rostral-caudal direction, further tamping and adjusting of cage final position under fluoroscopic guidance, retraction and removal of cage, and insertion of fusion or graft material.

EXAMPLES

The following non-limiting examples are provided to further illustrate embodiments of the invention disclosed herein. It should be appreciated by those of skill in the art that the techniques disclosed in the examples that follow represent approaches that have been found to function well in the practice of the invention, and thus can be considered to constitute an example of a mode for its practice. However, those of skill in the art should, in light of the present disclosure, appreciate that many changes can be made in the specific embodiments that are disclosed and still obtain a like or similar result without departing from the spirit and scope of the invention.

A device as illustrated in FIG. 1 is provided, along with a distractor tool as described herein and a disc removal tool as described herein. During a spine surgery procedure, following macroscopic discectomy, the distractor tool is inserted into the interbody space, and its pairs of blades are extended in the rostral-caudal and anterior-posterior directions to protect neural tissue (at the posterior region of the interbody space) and vascular structures (at the anterior region of the interbody space). The blades may be retracted back and no longer extended, as needed. The disc removal tool reaches the interbody space through the neck of the distractor tool, and is used to remove remaining disc and to potentially decorticate bone once distractor blades covering the endplates are removed in order to prepare a fusion bed. The disc removal tool is then removed.

The cage device is then inserted into the interbody space through the neck of the distractor tool with the blades of the distractor tool retracted to allow for proper placement of the cage device against the endplates, and mechanical force may be employed (e.g., through use of a mallet) to properly orient and position the device within the interbody space. Fluoroscopy may also be used to guide proper placement of the device. The device is then deployed in the anterior-posterior direction (by pushing down on a lever-handle on an inserter tool or other mechanism for deployment that is in mechanical communication with the device and its bridging structures) and lordotic expansion is achieved to the desired angle (by rotating a dial (e.g., a clicking dial) on the handle of or otherwise actuating the inserter tool to control the lordotic expander in the device) as described above. Proper placement is confirmed via fluoroscopy. If the position of the device is satisfactory, a mesh positioned around the cage is filled with graft or other fusion-promoting material, the device is then disengaged from the inserter tool (which is removed), and the distractor tool is then removed.

The various methods and techniques described above provide a number of ways to carry out the invention. This patent description pertains to any interbody device that is expandable in the anterior-posterior trajectory in situ and/or can achieve variable degrees of lordosis in situ, depending on the clinical indication. Of course, it is to be understood that not necessarily all objectives or advantages described may be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as may be taught or suggested herein. A variety of advantageous and disadvantageous alternatives are mentioned herein. It is to be understood that some preferred embodiments specifically include one, another, or several advantageous features, while others specifically exclude one, another, or several disadvantageous features, while still others specifically mitigate a present disadvantageous feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be mixed and matched by one of ordinary skill in this art to perform methods in accordance with principles described herein. Among the various elements, features, and steps some will be specifically included and others specifically excluded in diverse embodiments.

Although the invention has been disclosed in the context of certain embodiments and examples, it will be understood by those skilled in the art that the embodiments of the invention extend beyond the specifically disclosed embodiments to other alternative embodiments and/or uses and modifications and equivalents thereof.

Many variations and alternative elements have been disclosed in embodiments of the present invention. Still further variations and alternate elements will be apparent to one of skill in the art. Various embodiments of the invention can specifically include or exclude any of these variations or elements.

In some embodiments, the terms "a" and "an" and "the" and similar references used in the context of describing a particular embodiment of the invention (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided with respect to certain embodiments herein is intended merely to better illuminate the invention and does not pose a limitation on the scope of the invention otherwise claimed.

Preferred embodiments of this invention are described herein, including the best mode known to the inventors for carrying out the invention. Variations on those preferred embodiments will become apparent to those of ordinary skill in the art upon reading the foregoing description. It is contemplated that skilled artisans can employ such variations as appropriate, and the invention can be practiced otherwise than specifically described herein. Accordingly, many embodiments of this invention include all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

In closing, it is to be understood that the embodiments of the invention disclosed herein are illustrative of the principles of the present invention. Other modifications that can be employed can be within the scope of the invention. Thus, by way of example, but not of limitation, alternative configurations of the present invention can be utilized in accordance with the teachings herein. Accordingly, embodiments of the present invention are not limited to that precisely as shown and described.

What is claimed:

1. An apparatus, comprising:
   a first element having a top surface and a bottom surface configured to contact opposing bone surfaces, wherein the top and bottom surfaces each include a surface treatment, wherein the surface treatment reduces migration of the first element after insertion of the first element into a body;
   a second element;
   a first bridging structure in mechanical communication with both the first element and the second element, wherein upon actuation of the bridging structure, the first element and the second element separate from one another; and
   a lordotic expander associated with the first element, wherein upon actuation of the lordotic expander, a height of the first element in the rostralcaudal direction increases without increasing a height of the second element in the rostralcaudal direction, and actuation of the lordotic expander does not separate the first element from the second element.

2. The apparatus of claim 1, further comprising a second bridging structure in mechanical communication with both the first element and the second element, wherein upon actuation of the first and second bridging structures, the first element and the second element separate from one another.

3. The apparatus of claim 1, wherein the surface treatment is teeth, an adhesive or spikes.

4. The apparatus of claim 1, wherein the first element includes a top portion and a bottom portion.

5. The apparatus of claim 1, wherein the second element includes a top portion and a bottom portion.

6. A system for spine surgery, comprising:
   a device including a first element having a top surface and a bottom surface configured to contact opposing bone surfaces, wherein the top and bottom surfaces each include a surface treatment, wherein the surface treatment reduces migration of the first element after insertion of the first element into a body, a second element, a bridging structure in mechanical communication with both the first element and the second element, wherein upon actuation of the bridging structure, the first element and the second element separate from one another, and an expander connected to the first element, wherein upon actuation of the expander, a height of the first element in the rostralcaudal direction increases without increasing a height of the second element in the rostralcaudal direction;
   a bridging tool that interacts with the device to actuate the bridging structure to expand the device in the anterior-posterior direction in the spine; and
   an expander tool that interacts with the expander of the device to increase the height of the first element in the rostralcaudal direction to achieve lordosis without increasing the height of the second element in the rostralcaudal direction.

7. The system of claim 6, wherein the device is bullet-shaped.

8. The system of claim 6, wherein the expander is configured to be actuated by a screw threaded mechanism.

9. The system of claim 6, wherein the surface treatment promotes bony integration following insertion and deployment of the device in an intervertebral space.

10. The system of claim 9, wherein the surface treatment include spikes, teeth or an adhesive.

11. The system of claim 6, further comprising a distractor tool having a handle, wherein the device may be inserted into an intervertebral space through the handle of the distractor tool.

12. The system of claim 11, wherein the distractor tool includes an expansion mechanism attached to the handle, and the expansion mechanism expands or retracts in both the anterior-posterior direction and the rostralcaudal direction within an intervertebral space.

13. The system of claim 12, wherein the expansion mechanism further includes a first pair of blades to controllably expand or retract in the anteriorposterior direction, and a second set of blades to controllably expand or retract in the rostral-caudal direction.

14. The system of claim 6, further comprising a mesh structure incorporated within a space between the first element and the second element.

15. The system of claim 6, wherein the first element includes a top portion and a bottom portion.

16. The system of claim 6, wherein the second element includes a top portion and a bottom portion.

* * * * *